(12) United States Patent
Dasilva et al.

(10) Patent No.: US 6,451,009 B1
(45) Date of Patent: Sep. 17, 2002

(54) OCDR GUIDED LASER ABLATION DEVICE

(75) Inventors: Luiz B. Dasilva, Danville; Bill W. Colston, Jr., Livermore; Dale L. James, Tracy, all of CA (US)

(73) Assignee: The Regents of the University of California, Oakland, CA (US)

( * ) Notice: Subject to any disclaimer, the term of this patent is extended or adjusted under 35 U.S.C. 154(b) by 95 days.

(21) Appl. No.: 09/660,037

(22) Filed: Sep. 12, 2000

(51) Int. Cl.$^7$ ............................................. A61B 18/18
(52) U.S. Cl. ............................ 606/12; 606/11; 356/481
(58) Field of Search ...................... 356/481; 606/10–12

(56) References Cited

U.S. PATENT DOCUMENTS

| | | | |
|---|---|---|---|
| 5,321,501 A | 6/1994 | Swanson et al. | 356/345 |
| 5,459,570 A | 10/1995 | Swanson et al. | 356/345 |
| 5,570,182 A | 10/1996 | Nathel et al. | 356/345 |
| 6,175,669 B1 * | 1/2001 | Colston et al. | 356/511 |
| 6,228,076 B1 * | 5/2001 | Winston et al. | 606/12 |
| 6,330,063 B1 * | 12/2001 | Knuettel et al. | 356/479 |

OTHER PUBLICATIONS

B.L. Danielson et al, *Guided–Wave Reflectometry with Micrometer Resolution*, Applied Optics, vol. 26, No. 14, Jul. 15, 1987.

M.J. Everett et al, *Birefringence Characterization of Biological Tissue by Use of Optical Coherence Tomography*, Optics Letters, vol. 23, No. 3, Feb. 1, 1988.

R.C. Youngquist et al, *Optical Coherence–Domain Reflectometry: A New Optical Evaluation Technique*, Optical Letters, vol. 12, No. 3, Mar. 1987.

X. Clivaz et al, *High–Resolution Reflectometry in Biological Tissues*, Optics Letters, vol. 17, No. 1, Jan. 1, 1992.

M.R. Hee et al, *Polarization–Sensitive Low–Coherence Reflectometer for Birefringence Characterization and Ranging*, J.Opt.Soc.Am.B., vol. 9, No. 6, Jun. 1992.

G.J. Tearney et al, *Scanning Single–Mode Fiber Optic Catheter–Endoscope for Optical Coherence Tomography*, Optics Letters, vol. 21, No. 7, Apr. 1996.

\* cited by examiner

Primary Examiner—Linda C. M. Dvorak
Assistant Examiner—Henry Johnson, III
(74) Attorney, Agent, or Firm—L. E. Carnahan; Alan H. Thompson

(57) ABSTRACT

A guided laser ablation device. The device includes a mulitmode laser ablation fiber that is surrounded by one or more single mode optical fibers that are used to image in the vicinity of the laser ablation area to prevent tissue damage. The laser ablation device is combined with an optical coherence domain reflectometry (OCDR) unit and with a control unit which initializes the OCDR unit and a high power laser of the ablation device. Data from the OCDR unit is analyzed by the control unit and used to control the high power laser. The OCDR images up to about 3 mm ahead of the ablation surface to enable a user to see sensitive tissue such as a nerve or artery before damaging it by the laser.

17 Claims, 2 Drawing Sheets

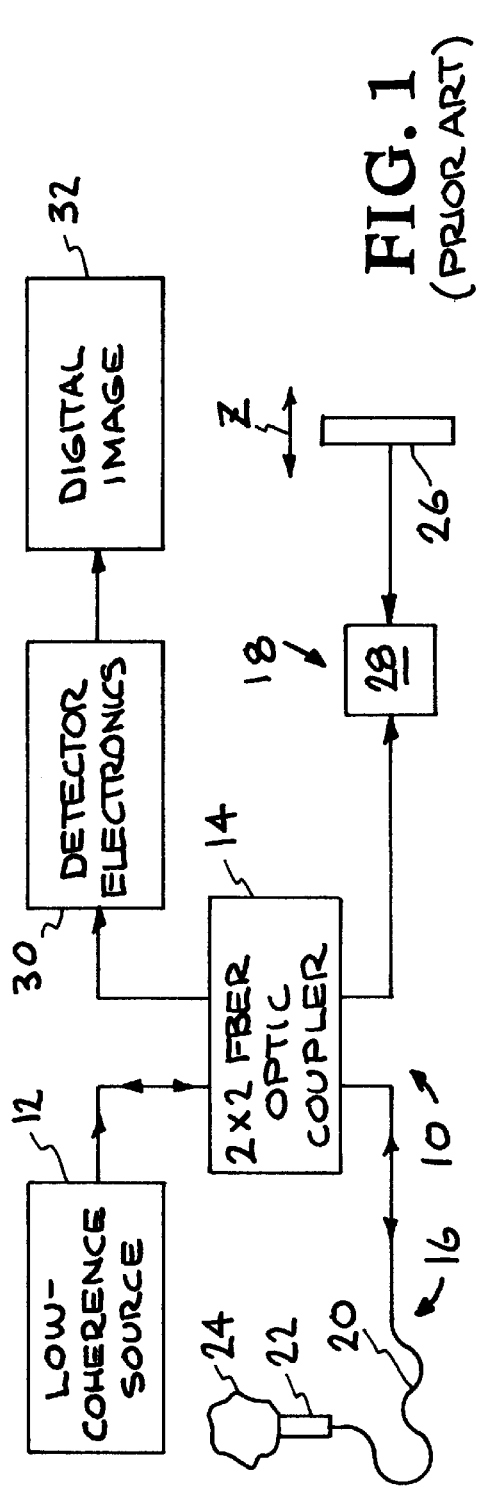
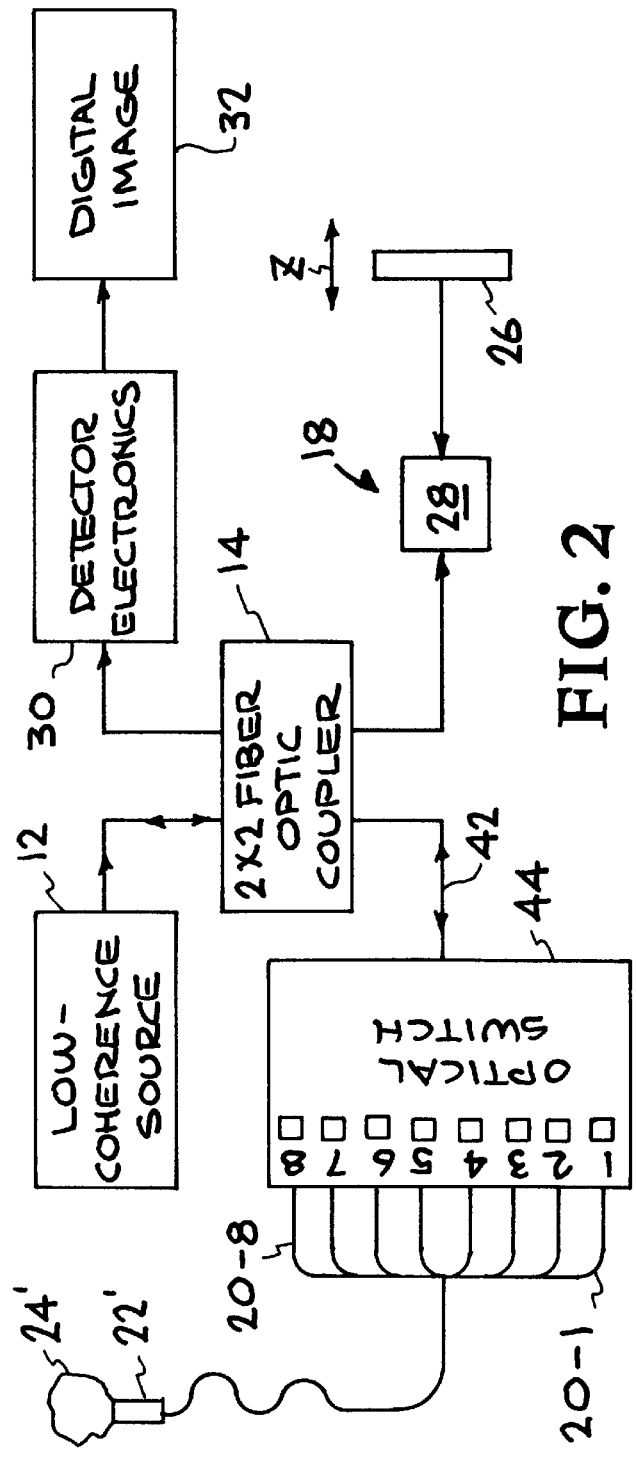

OCDR GUIDED LASER ABLATION DEVICE

The United States Government has rights in this invention pursuant to Contract No. W-7405-ENG-48 between the United States Department of Energy and the University of California for the operation of Lawrence Livermore National Laboratory.

BACKGROUND OF THE INVENTION

The present invention is directed to the removal and repair of tissue, particularly to the treatment or removal of tissue by laser ablation, and more particularly to a laser ablation device combined with an optical coherence domain reflectometry (OCDR) unit to provide an image of the ablation area, particularly in front of the ablation surface, whereby the laser ablation device can be safety guided by a user or can be shut off if too close to sensitive tissue.

Laser tissue ablation has been used for many years in medicine and is now starting to find important applications in dentistry. Laser ablation offers the potential of precision cutting with minimal collateral damage and with coagulation. Lasers have been used with good results to cut soft tissue (muscle, fat, cornea) and hard tissue (teeth, bone). However, a need has existed for some form of control mechanism that could control laser ablation and if necessary stop it before causing tissue damage. Prior approaches to this need has been the use of fluorescence spectroscopy or other optical techniques but these prior techniques only probe near the surface and have little sensitivity to tissue type below the surface.

The present invention provides a solution to the above mentioned need by providing a laser ablation device which can either image for a user the surface area and an area in front of the surface area or function to shut off the laser when a certain distance from sensitive tissue (nerve or artery) is determined. Basically, the present invention involves a laser ablation unit, which includes a high power laser, an optical coherence domain reflectometry (OCDR) unit, and a control unit.

As known in the art, optical coherence domain reflectometry (OCDR) is a technique developed by Younquist et al. in 1987 (Youngquist, R. C. et al., "Optical Coherence-Domain Reflectometry: A New Optical Evaluation Technique," 1987, Optics Letters 12 (3):158–160). Danielson et al. (Danielson, B. L. et al., "Guided-Wave Reflectometry with Micrometer Resolution," 1987, Applied Physics 26(14): 2836–2842) also describe an optical reflectometer which uses a scanning Michelson interferometer in conjunction with a broadband illuminating source and cross-correlation detection. OCDR was first applied to the diagnosis of biological tissue by Clivaz et al. in January 1992 (Clivaz, X. et al., "High-Resolution Reflectometry in Biological Tissues," 1992, Optics Letters 17(1):4–6). A similar technique, optical coherence tomography (OCT), has been developed and used for imaging with catheters by Swanson et al. in 1994 (Swanson, E. A. et al., U.S. Pat. Nos. 5,321,501 and 5,459,570). Tearney et al. (Tearney, G. J. et al., "Scanning Single-Mode Fiber Optic Catheter-Endoscope for Optical Coherence Tomograph," 1996, Optics Letters 21(7):543–545) also describe an OCT system in which a beam is scanned in a circumferential pattern to produce an image of internal organs. U.S. Pat. No. 5,570,182 to Nathel et al. describes method and apparatus for detection of dental caries and periodontal disease using OCT. However, as OCT systems relay on mechanical scanning arms, miniaturizing them enough to leave room for other devices in the catheter is a serious problem.

Polarization effects in an OCDR system for birefringence characterization have been described by Hee et al. (Hee, M. R. et al., "Polarization-sensitive low-coherence reflectometer for birefringence characterization and ranging," J. Opt. Soc. Am. B, Vol. 9, No. 6, June 1992, 903–908) and in an OCT system by Everett et al. (Everett, M. J. et al., "Birefringence characterization of biological tissue by use of optical coherence tomography," Optics Letters, Vol. 23, No. 3, Feb. 1, 1998, 228–230).

In a prior art OCDR scanning system 10, shown in FIG. 1, light from a low coherence source 12 is input into a 2×2 fiber optic coupler 14, where the light is split and directed into sample arm 16 and reference arm 18. An optical fiber 20 is connected to the sample arm 16 and extends into device 22, which scans an object 24. Reference arm 18 provides a variable optical delay. Light input into reference arm 18 is reflected back by reference mirror 26. A piezoelectric modulator 28 maybe induded in reference arm 18 with a fixed mirror 26, or modulator 28 may be eliminated by scanning mirror 26 in the Z-direction. The reflected reference beam from reference arm 18 and a reflected sample beam from sample arm 16 pass back through coupler 14 to detector 30 (including processing electronics), which processes the signals by techniques that are well known in the art to produce a backscatter profile (or "image") on display 32.

The potential of the OCDR guided laser ablation device of this invention has been experimentally demonstrated to provide the potential for a range of clinical applications including OCDR guided caries ablation, OCDR guided treatment of periodontal diseases, and OCDR guided surgery.

SUMMARY OF THE INVENTION

It is an object of the present invention to provide an improved laser ablation device for both soft and hard tissue.

A further object of the invention is to provide a device for imaging both the surface of a laser ablation area and an area in front of the ablation surface.

A further object of the invention is to provide an optical coherence domain reflectometry (OCDR) guided laser ablation device.

Another object of the invention is to provide a device which combines the effectiveness of laser ablation with an imaging device to enable a user to visualize the tissue in front of an ablation surface.

Another object of the invention is to provide an improved laser application device which combines the use of a high power laser, an OCDR unit, and a control unit, whereby the tissue in front of the ablation surface may be imaged by a user or analyzed to initiate an alarm or shut off the laser when a predetermined distance from the ablation surface to sensitive tissue (e.g., nerve, artery, etc.) is reached, or in dentistry when the diseased enamel or dentin in the caries has all been removed.

Other objects and advantages of the present invention will become apparent from the following description and accompanying drawings. Basically the invention involves an OCDR guided laser ablation device. The invention includes a multimode laser ablation fiber or tool that is surrounded by a plurality of (or only one) single mode optical fibers, the ablation fiber is operatively connected to a high power laser and the optical fibers are operatively connected to an OCDR unit, the high power laser and OCDR unit being connected to a control unit. The optical fibers function via the OCDR unit to image the ablation area, which includes the ablation surface and the areas in front of the ablation surface, that front area being 3 mm deep for example. The surrounding 1, 2, 4 or more single mode optical fibers independently couple light from the sample arm of the OCDR to the tissue being or to be ablated. Light from these fibers exit the tip and are directed into the hard or soft tissue via small diameter optics (such as gradient index lenses and prisms). The light reflected or back-scattered from the tissue is then collected by the same optical fibers and detected by the OCDR unit. This detected information is translated into a profile image of the tissue optical properties near the ablation surface. This information can be displayed on a monitor for the users visual observation or analyzed by computer software to sound an alarm or stop the ablation laser when a selected boundary or distance to sensitive tissue is reached. The device of this invention could use multiple OCDR units (one for each imaging fiber, or used with a form of multiplexer. Thus, the device could be set to sound an alarm or be turned off when the ablation surfaces reaches within 500 microns of an artery wall, for example, or in dentistry when the diseased enamel or dentin in the caries has all been removed. Thus, the present invention has a range of clinical applications including OCDR.

BRIEF DESCRIPTION OF THE DRAWINGS

The accompanying drawings, which are incorporated into and form a part of the disclosure, illustrate an embodiment of the invention and, together with the description, serve to explain the principles of the invention.

FIG. 1 is a prior art OCDR scanning system.

FIG. 2 is a schematic diagram of an OCDR system for catheter guidance and optical sensing with multiplexed sample arm.

DETAILED DESCRIPTION OF THE INVENTION

The present invention is directed to an improved laser ablation device, wherein tissue to be ablated, up to about 3 mm in front of the ablation surface, is imaged for example, whereby damage to sensitive tissue such as a nerve or artery, for example, can be prevented. In addition to, or instead of, enabling a user too see the sensitive tissue, the information can be analyzed by computer software and produce an alarm or send a signal to stop the ablation laser, as decided by the user. For example, the device through computer software could be commanded to turn off the laser when the ablation surface reaches within 500 microns of an artery wall, or when the diseased enamel or dentin in the caries has been removed. Thus, the invention can be used to cut soft tissue (muscle, fat, cornea) and hard tissue (teeth, bone). The overall device of the present invention includes a laser ablation tool or multimode fiber or hollow waveguide surrounded by a plurality of single mode optical fibers, the multimode fiber being connected to a high power laser and the plurality of optical fibers are connected to one or more OCDR units or to a single OCDR unit via a multiplexer. The OCDR unit (s) and the high power laser are connected to a control unit which initializes the OCDR unit and high power laser, and data from the OCDR is analyzed by the control unit and used to control the high power laser. The optical fibers can be mounted so as to couple light from the OCDR to different areas of the ablation field and to reflect different areas of the ablation field and/or ablation surface to the OCDR. The optical fiber tips are provided with small diameter optics (such as gradient index lenses and prisms). The OCDR unit translates the reflected information into a profile image of the tissue optical properties near the ablation surface.

Figure 3:
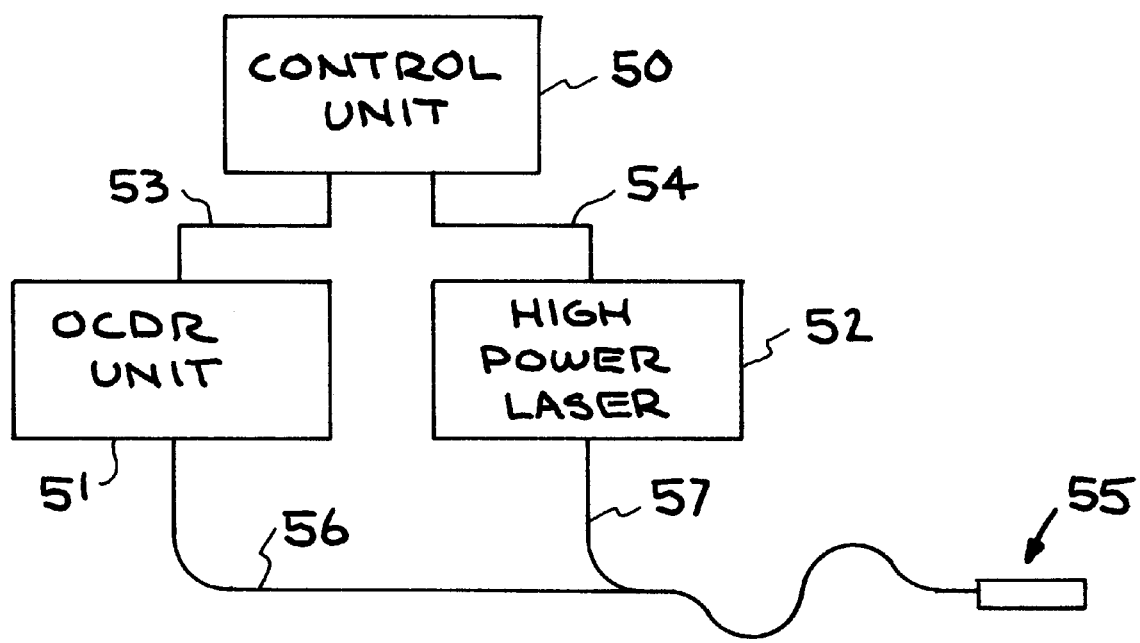
FIG. 3 illustrates the main components of the OCDR guided laser ablation device including a multimode laser tool or fiber made in accordance with the present invention.
Figure 4:
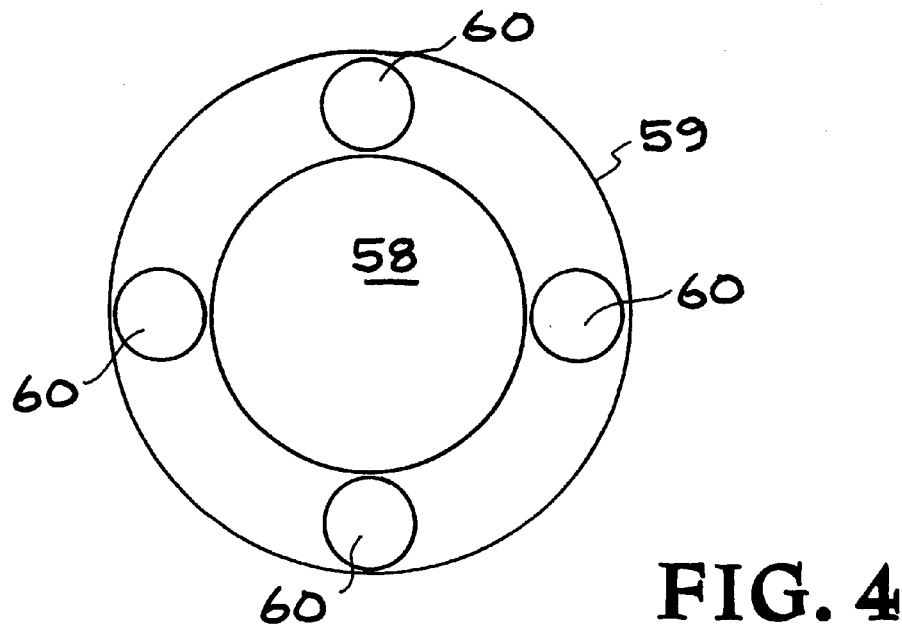
FIG. 4 illustrates an enlarged end view of the ablation device of FIG. 3, showing the tool being composed of a multimode laser ablation fiber surrounded by a plurality of single mode optical fibers.

Referring now to the drawings, FIG. 1 having been previously described, FIG. 2 schematically illustrate an embodiment of the OCDR guided laser ablation system with the OCDR having been multiplexed, with FIG. 3 illustrating the overall device or system, and FIG. 4 illustrating an end view of the ablation tool.

The device guidance and optical sensing system 40 is illustrated in FIG. 2. The device is based on an optical coherence domain reflectometer (OCDR) which has been multiplexed. Except for the multiplexed feature, the system is similar to the prior art system 10 of FIG. 1 and similar components have been given similar reference numerals. Output from a low coherence light source 12 is split at the 2×2 fiber optic coupler 14 and directed through a multiplexed sample arm 42 toward the ablation area 24' and through a reference arm 18 to reference mirror 26. Reflections from the mirror 26 and backscattered light from the ablation area 24' are recombined at the coupler 14 and propagated to the detector 30 (and light source 12). Constructive interference creates a signal at the detector 30 when the sample and reference reflections have traveled approximately the same optical group delay. The shorter the coherence length of the source, the more closely the sample and reference arm group delays must be matched for constructive interference to occur. By imposing a changing optical delay in the reference arm 18 with a known velocity, either by scanning mirror 26 in the Z-direction or with a piezo-modulator 28 (with fixed mirror 26), the amplitudes and longitudinal positions of reflections from the ablation area 24' can be measured with high precision. The sample arm 42 contains a multiplexer 44 for switching between several (e.g., 8) optical fibers 20-1 . . . 20-8, allowing sequential spatially distinct regions to be diagnosed consecutively using the same basic OCDR system. The fibers can be placed anywhere in the device or tool, 22.

The overall OCDR guided laser ablation system as shown in FIG. 3 comprises a control unit 50 operatively connected to an OCDR unit 51 and a high power laser 52 via connections indicated at 53 and 54. By way of example the laser 52 may be of a Nd-YAG laser, Er-YAG, or $CO_2$ laser, either pulsed or CW with typical power-levels of less than 50 watts. Each of the OCDR unit 51 and laser 52 is operatively connected to an ablation tool or instrument generally indicated at 55, as indicated at 56 and 57. The ablation tool or instrument 55, as shown in FIG. 4 includes a multimode fiber or waveguide 58 surrounded by a member 59 in which a plurality, four in this embodiment, of single mode optical fibers 60 are equally spaced around the control fiber 58. While not shown, the optical fibers 60 are provided at the distal end or tip with optics, such as gradient index lenses or prisms, and may each be mounted in member 59 so as to be directed to a different area of the ablation field 24' of FIG. 2.

While the embodiment of FIG. 2 utilizes a multiplexer (optical switch 44), each of the imaging fibers 60 could be connected to a separate OCDR unit. Alternatively, each fiber length could vary by some fraction of the scan length of a single OCDR system. For example, a 10 mm scanner could collect data from two fibers that differ in length by 5 mm.

Whereby the first 5 mm of data collected can be assumed to be from the short probe fiber and the second 5 mm of data can be assumed to be from the longer probe fiber. Several alternative embodiments of the OCDR system may be utilized, including a doppler OCDR, a birefringence sensitive OCDR, and a color OCDR, to enhance the contrast of the multiplexed OCDR of FIG. 2 and obtain other useful clinical information. Doppler OCDR, which provides a measurement of scatterer movement as a function of axial position, can be used to quantify blood flow in the gingival tissue and is potentially an indirect method for assessing soft tissue vitality. The birefrigence of both hard and soft tissue structures in the oral cavity can be measured using a birefringence-sensitive OCDR system, and is potentially useful for locating decalcified or carious regions in the tooth. A birefrigence-sensitive OCT system has been constructed and which measured birefrigence of several biological tissues. Color OCDR makes use of multiple wavelengths to spectroscopically resolve tissue microstructures based on their wavelength dependent absorption or scattering properties. A dual-wavelength OCDR system has been built and used to measure water concentrations in turbid scattering phantoms.

The OCDR guided laser ablation device of this invention has the potential for a range of clinical applications, including the following; 1) OCDR guided caries ablation when the device is used to safely guide laser ablation or caries with minimal damage to viable dental tissue; 2) OCDR guided treatment of periodontal diseases which enables an imaging diagnostic that can image the extent of thermal damage to tissue; and 3) OCDR guided surgery by providing imaging ahead of the ablation area which allows surgeons to detect the presence of nerves, arteries and other delicate tissue before it is ablated. Thus, the OCDR guided laser ablation device of this invention provides a significant advance in the field of laser tissue ablation.

While particular embodiments, parameters, etc. have been described and/or illustrated to exemplify and explain the principle of the invention such are not intended to be limited. Modifications and changes may become apparent to those skilled in the art, and it is intended that the invention be limited only by scope of the appended claims.

What is claimed is:

1. In a laser ablation device, the improvement comprising: means including an optical coherence domain reflectometry (OCDR) system for providing information relative to material located in front of an ablation surface,
   said means includes a plurality of spaced optical fibers positioned adjacent the ablation surface and operatively connected to said OCDR system.

2. The improvement of claim 1, wherein said means includes a control unit operatively connected to said OCDR system for controlling laser energy directed to the ablation surface.

3. In a laser ablation device, the improvement comprising:
   means including an optical coherence domain reflectometry (OCDR) system for providing information relative to material located in front of an ablation surface,
   said means includes an ablation tool and a plurality of equally spaced optical fibers being mounted in said tool and operatively connected to said OCDR system.

4. The improvement of claim 3, wherein said ablation tool includes a member selected from the group consisting of a multiple mode fiber and a waveguide.

5. The improvement of claim 3, wherein said plurality of spaced optical fibers are connected to said OCDR system via a multiplexer.

6. The improvement of claim 5, said multiplexer comprises an optical switch.

7. The improvement of claim 1, wherein said OCDR system includes at least one OCDR unit operatively connected to said plurality of optical fibers.

8. An optical coherence domain reflectometry (OCDR) guided laser ablation device, comprising:
   a control unit,
   an OCDR unit operatively connected to said control unit,
   a high power laser operatively connected to said control unit,
   an ablation tool operatively connected to said high power laser and to OCDR unit,
   said ablation tool including a plurality of optical fibers operatively connected to said OCDR unit.

9. The laser ablation device of claim 8, wherein said ablation tool includes a member connected to said laser and composed of one of the group consisting of a multimode fiber and a waveguide.

10. The laser ablation device of claim 8, wherein said plurality of optical fibers are connected to said OCDR unit via a multiplexer.

11. The laser ablation device of claim 8, wherein said ablation tool additionally includes a member connected to said laser, and wherein said plurality of optical fibers are equally spaced about said member.

12. The laser ablation device of claim 11, wherein said multiplexer comprises an optical switch.

13. The laser ablation device of claim 8, wherein light reflected through said ablation tool to said OCDR unit is translated by said OCDR unit into a profile scan or image of the optical properties of the material adjacent an ablation surface, and wherein said laser ablation device includes means for processing the profile image selected from the group consisting of a image display, an alarm, or laser shutdown mechanism.

14. The laser ablation device of claim 8, wherein said ablation tool includes a multimode fiber connected to said laser and surrounded by four optical fibers connected to said OCDR unit.

15. The laser ablation device of claim 14, wherein said optical fibers are connected through a multiplexer to said OCDR unit.

16. The laser ablation device of claim 8, in combination with one of a doppler OCDR, a birefringence-sensitive OCDR, and a color OCDR.

17. The laser ablation device of claim 8, wherein said plurality of optical fibers have different lengths.

* * * * *